United States Patent
Hui et al.

(10) Patent No.: US 7,204,960 B2
(45) Date of Patent: Apr. 17, 2007

(54) APPARATUS AND METHOD FOR CALIBRATION OF A DISPENSING SYSTEM

(75) Inventors: Hon Chiu Hui, Kwai Chung (CN); Wing Fai Lam, Kwai Chung (CN); Lim Pun Kong, Kwai Chung (CN); Ka Yee Mak, Kwai Chung (CN); Ka Yin Lee, Kwai Chung (CN)

(73) Assignee: ASM Assembly Automation Ltd. (SG)

( * ) Notice: Subject to any disclaimer, the term of this patent is extended or adjusted under 35 U.S.C. 154(b) by 620 days.

(21) Appl. No.: 10/379,832

(22) Filed: Mar. 3, 2003

(65) Prior Publication Data

US 2004/0175832 A1     Sep. 9, 2004

(51) Int. Cl.
  B01L 3/02       (2006.01)
  B32B 5/02       (2006.01)
  G01N 21/00      (2006.01)
  G01N 31/00      (2006.01)
  G01F 19/00      (2006.01)

(52) U.S. Cl. .......................... 422/82.05; 100/55; 436/8; 436/180; 436/148; 436/164; 73/1.73; 73/1.74

(58) Field of Classification Search .................. 422/50, 422/55, 100, 68.1, 82.05, 82.09; 436/180, 436/43, 148, 164, 171, 8; 73/1.73, 1.74
See application file for complete search history.

(56) References Cited

U.S. PATENT DOCUMENTS

| | | | |
|---|---|---|---|
| 5,114,350 A * | 5/1992 | Hewett | 435/286.4 |
| 5,482,861 A * | 1/1996 | Clark et al. | 436/48 |
| 5,906,682 A | 5/1999 | Bouras et al. | 118/712 |
| 6,232,072 B1 * | 5/2001 | Fisher | 435/6 |
| 6,412,328 B1 | 7/2002 | Cavallaro et al. | 73/1.74 |
| 6,558,623 B1 * | 5/2003 | Ganz et al. | 422/63 |
| 6,579,497 B2 * | 6/2003 | Woodward | 422/66 |
| 6,589,792 B1 * | 7/2003 | Malachowski | 436/63 |
| 6,599,476 B1 * | 7/2003 | Watson et al. | 422/63 |
| 6,821,484 B1 * | 11/2004 | Gregersen | 422/73 |
| 6,902,703 B2 * | 6/2005 | Marquiss et al. | 422/100 |
| 6,926,866 B2 * | 8/2005 | Sickinger et al. | 422/100 |
| 6,943,036 B2 * | 9/2005 | Bass | 436/180 |
| 2003/0049863 A1 * | 3/2003 | Woodward | 436/180 |
| 2003/0113233 A1 * | 6/2003 | Nanthakumar | 422/100 |
| 2003/0124028 A1 * | 7/2003 | Carlson et al. | 422/68.1 |
| 2003/0124735 A1 * | 7/2003 | Nanthakumar et al. | 436/180 |
| 2004/0022689 A1 * | 2/2004 | Wulf et al. | 422/100 |
| 2004/0062686 A1 * | 4/2004 | Ganz et al. | 422/100 |
| 2005/0095723 A1 * | 5/2005 | DiTrolio et al. | 436/180 |

* cited by examiner

Primary Examiner—Brian R. Gordon
(74) Attorney, Agent, or Firm—Ostrolenk, Faber, Gerb & Soffen, LLP (57) ABSTRACT

The invention provides an apparatus and method for calibrating a dispensing system. A dispenser dispenses a controlled quantity of material into a container for receiving material. A system, preferably a vision system comprising an image capturing device and an imaging system, is adapted to capture an image of a physical dimension of a quantity of dispensed material in a given time. The physical dimension may be a width of a top surface area, a height or a cross-sectional area of the dispensed material. A calibrating system is adapted to calculate a volume of the quantity of material based upon said physical dimension.

42 Claims, 6 Drawing Sheets

1st measuring point        2nd measuring point

APPARATUS AND METHOD FOR CALIBRATION OF A DISPENSING SYSTEM

FIELD OF THE INVENTION

The invention relates to dispensing systems used in the semiconductor industry, and in particular, to the calibration of dispensing systems for more accurate and precise dispensation of material from dispensers.

BACKGROUND AND PRIOR ART

Dispensing systems are used widely in the semiconductor industry for a range of applications. These applications include underfill processes, encapsulation and dispensing of adhesive substances onto circuit boards for mounting components. Accuracy and precision of dispensing is becoming more important because sizes of semiconductor packages are gradually decreasing. In addition, automated measurement and adjustment of dispensed quantities with computerized control systems is becoming the norm to reduce human intervention and increase speed. As a result, accurate automated calibration systems are required.

For example, U.S. Pat. No. 5,906,682 for a "Flip Chip Underfill System and Method" discloses a calibration system which collects and measures an amount of material dispensed during a calibration routine against a target quantity. The weight of dispensed material at a given time is measured with weighing scales in order to adjust the dispensing system to achieve the target quantity. However, weighing scales are sensitive to changes in temperature so that the measured weight may vary with the temperature of air or the temperature of the sample. When small amounts of material are dispensed, such as to the order of 2 mg, such sensitive scales are only available at a relatively high cost. Furthermore, material used in a dispensing process is conventionally polymeric and fluid by nature, and measured in terms of cavity volume of encapsulation in a device, rather than in terms of units of weight. Although weight can be converted into volume for a specific type of material, the specific gravity of polymeric material will vary in space, resulting in dispensing errors in addition to the errors inherent upon conversion.

Another example is U.S. Pat. No. 6,412,328 entitled "Method and Apparatus for Measuring the Size of Drops of a Viscous Material Dispensed from a Dispensing System". It discloses a dispensing apparatus having a housing, a dispenser that dispenses a quantity of viscous material, a measuring apparatus having a bottom plate to receive the viscous material, a top plate that is positioned over the bottom plate after the viscous material has been dispensed, and a compressing apparatus that compresses the material between the top and bottom plates. The quantity of material dispensed is determined by viewing the compressed material, and then multiplying the area of the compressed material by the distance between the two plates, which may be equivalent to the height of a gap shim between the two plates.

This method is time-consuming, in that mechanical manipulation of the various devices during calibration results in the wastage of a large proportion of calibration time. These steps of mechanical manipulation, including placement of a top pressure glass slide and plate by the dispensing system, locking using force rods, further compression of the plates with an air cylinder and finally the measurement by a viewing system are complicated. Thus, productivity lost from increased operation time of the dispensing device.

A further problem with the above prior art dispensing systems is that they are limited to calibration of a dispenser adapted for dot dispensing. Other modes of dispensation, such as line dispensing cannot be properly simulated and worked using this tool. Most of the dispensing systems used in surface mount technology require line dispensing within a heated environment, such as dam-fill encapsulation and flip-chip under-filling. Thus, the above methods do not provide an optimal solution to dispensing system calibration in a real environment.

SUMMARY OF THE INVENTION

It is an object of the invention to seek to provide an improved apparatus and method for calibration of a dispensing system without some of the aforesaid disadvantages of the prior art.

According to a first aspect of the invention there is provided apparatus for calibrating a dispensing system, comprising a dispenser for dispensing a controlled quantity of material, a container for receiving material, a system adapted to capture an image of a physical dimension of a quantity of dispensed material in a given time, and a calibrating system adapted to calculate a volume of the quantity of material based upon said physical dimension.

According to a second aspect of the invention there is provided a method for calibrating a dispensing system, comprising the steps of dispensing a controlled quantity of material into a container, capturing an image of a physical dimension of a quantity of material in the container in a given time, and processing the image to calculate a volume of the quantity of material in the container based upon said physical dimension.

It will be convenient to hereinafter describe the invention in greater detail by reference to the accompanying drawings which illustrate one embodiment of the invention. The particularity of the drawings and the related description is not to be understood as superseding the generality of the broad identification of the invention as defined by the claims.

DETAILED DESCRIPTION OF THE PREFERRED EMBODIMENT

Figure 1:
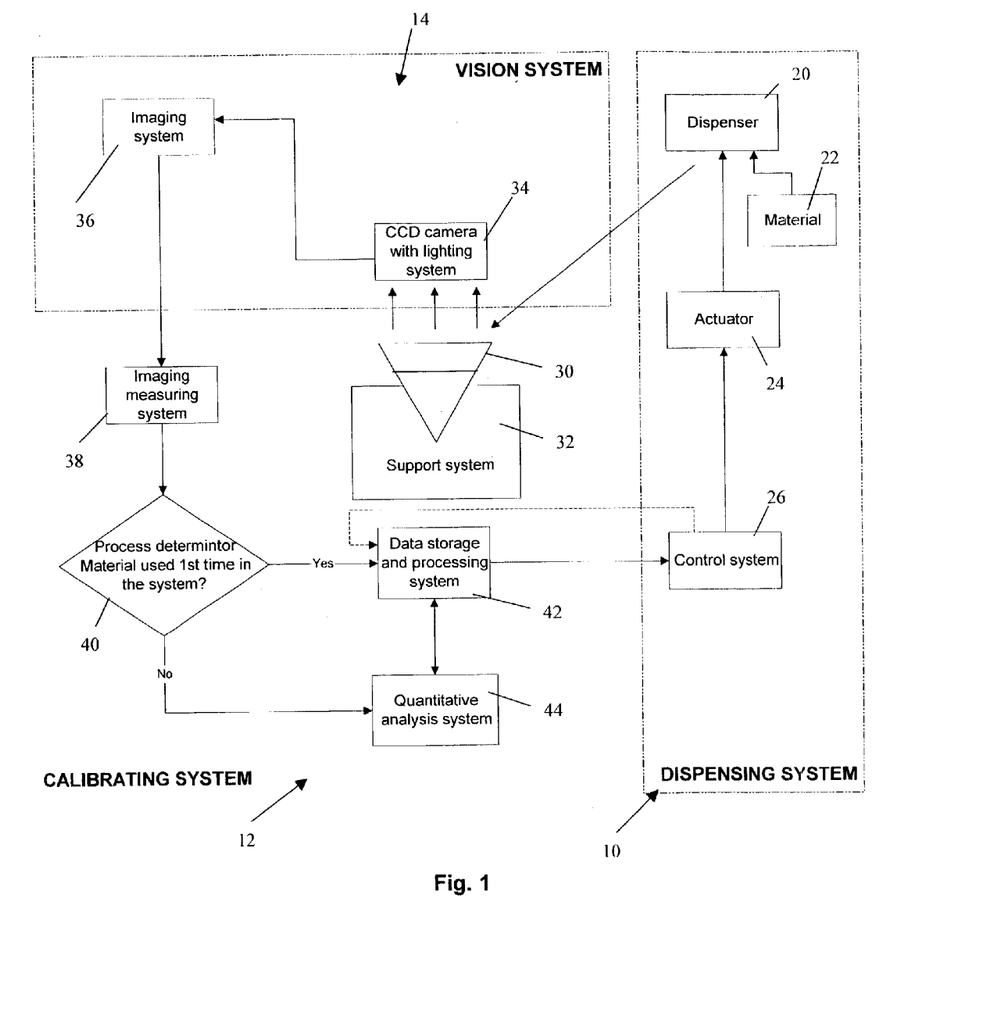
FIG. 1 is a schematic illustration of the relationship between a dispensing system, calibrating system and vision system according to a preferred embodiment of the invention.
Figures 2A, 2B:
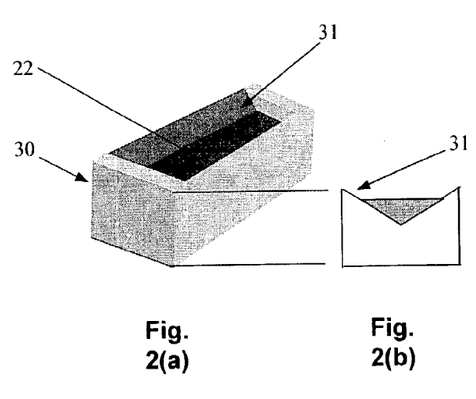
FIGS. 2(a), 2(b), 2(c) and 2(d) are respectively isometric and cross-sectional views of rectangular-shaped containers that may be used with the invention.
Figure 2C:
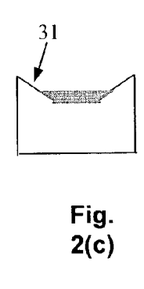
Figure 2D:
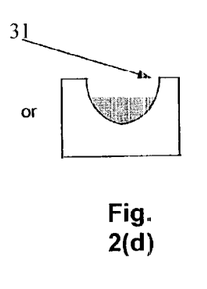

FIG. 1 is a schematic illustration of the relationship between a dispensing system 10, calibrating system 12 and vision system 14 according to a preferred embodiment of the invention. The dispensing system 10 includes a dispenser 20 for dispensing a controlled quantity of material 22 onto a substrate such as a printed circuit board. An actuator 24 induces flow of material 22 using pressure valves or other mechanisms. These mechanisms are monitored and adjusted with a computerized control system 26, so that the dispenser 20 may extrude a stable and controlled volume of material 22 based upon feedback. Flow-rates from the dispenser 20 may be automatically controlled using the control system 26. Although the invention may be implemented with more than one dispenser 20, only one dispenser 20 is illustrated in FIG. 1 for simplicity.

During calibration, the dispenser 20 extrudes a quantity of material 22 such as underfill or fill material into a material-receiving cavity of a shaped container 30 of the calibrating system 12, which is supported by a support system 32. The shaped container 30 is designed such that a volume of any given quantity of material 22 can be determined by observing a physical dimension of the material 22 (such as its width, height and/or cross-sectional area) in the shaped container at a certain position. Preferably, this is at a position directly over the shaped container 30 to view a top surface area of the dispensed material 22. An image capturing device, which may be in the form of a CCD camera 34, is placed over the container to capture images of the material in the shaped container 30. Measurements of dispensed material 22 are preferably continuously looped in the calibrating system 12 to provide continuous feedback to the control system 26 to control the flow of material 22 from the dispenser 20 in real time.

The CCD camera 34 feeds captured images to an imaging system 36, after which the images are processed by an imaging measuring system 38 to determine the width and length of the dispensed materials, expressed in units of pixel. The height of the dispensed material 22 within the container may further be measured by a laser displacement sensor 80, or alternatively, a second CCD camera 35 (see FIG. 7). Another embodiment of the present invention includes calculating the height of the material 22 by using experimental data comparing sets of width and length corresponding to predetermined heights of the material 22. These data comprising height, width and length of dispensed material will be transmitted to a data storage and processing system 42 or quantitative analysis system 44 governed by a process divider, namely a process determinator 40 deciding whether a type of material 22 has been utilized in this implementation before.

The process determinator 40 checks whether a type of material 22 is being used for the first time in the system. If it is being used for the first time, the data storage and processing system 42 will be triggered for data statistical processes, storage, dimensional calculation and calculation of dispensing control parameters. Data statistical processes include statistical algorithms to calculate a width of dispensed material and calculation of dimensions including the height of the dispensed material in the shaped container 30, wherein all results will be stored on storage means associated with the data storage and processing system 42. This step is particularly designed to teach the system to learn the surface tension between the dispensed material 22 and walls of the shaped container 30. The volume of dispensed material 22, will also be calculated in the quantitative analysis system 44 according to data concerning width, height and length of the dispensed material 22 with algorithms dependent upon the dimensions of the shaped container 30. The determined volume will further be converted into dispensing control parameters to achieve a desired flow-rate of material 22 to be dispensed. The control system 26 will receive these parameters and control the dispenser 20 and a gantry table 52 (see FIG. 4) to dispense the desired quantity. For example, the volume of material 22 dispensed will be decreased as the traveling speed of the gantry table 52 is increased.

The CCD camera 34 is responsible for capturing images and sending them to the image measuring system 38, whereby to determine the dispensed quantity in terms of width and length. Following further signal transmissions to the process determiner 40 which determines whether the fluid material 22 is new, either the data storage and processing system 42 or quantitative analysis system 44 will be triggered sequentially according to the decision of the process determiner 40.

If the material 22 is not being used for the first time in the system, and there is already a record in the data storage and processing system 42, the data is sent directly to the quantitative analysis system 44. The volume of dispensed material 22 may be directly calculated in the quantitative analysis system 44 according to measured width and length data, as well as using the records of corresponding heights that have been stored in the data storage and processing system 42. The algorithms for quantitative analysis are dependent upon the dimensions of the shaped container 30. The determined volume will further be converted into the dispensing control parameter in terms dispensing speed of the dispenser 20 and traveling speed in millimeters per second for the gantry table 52 as described above.

FIGS. 2(a), 2(b), 2(c) and 2(d) are respectively isometric and cross-sectional views of rectangular-shaped containers 30 that may be used with the invention. Each rectangular-shaped container 30 comprises cavities 31, preferably with sloping walls. The cavity 31 may be created using a cross-sectional shape, such as a polygon or a hemisphere, cut horizontally across a solid block. Ends of the shaped container will have to be walled-off using a non-opaque wall. A wall would preferably be attached to the side of the shaped container 30. A shape of the trapped material 22 is defined by the shape of the cavity 31, and the volume of material 22 is determinable from known dimensions of the cavity 31.

As material 22 is dispensed into the cavity 31, its cross-sectional area within the cavity 31 (laterally viewed from an end of the cavity) increases. By measuring its cross-sectional area, the quantity of material 22 dispensed can thus be determined using a mathematical formula. As illustrations, the base of the cavity can be pointed (FIG. 2(b)), flat (FIG. 2(c)) or curved (FIG. 2(d)).

Figures 3A, 3B:
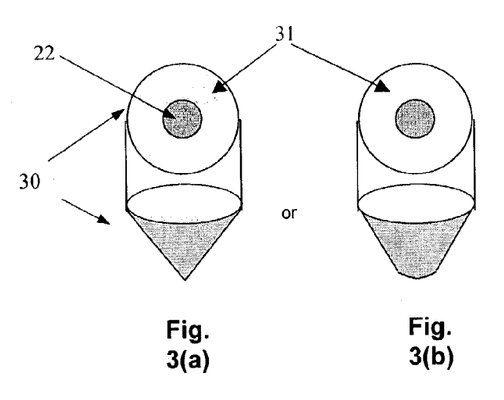
FIGS. 3(a) and 3(b) are top and side views respectively of conical-shaped and frusto-conical containers that may be used with the invention.

FIGS. 3(a) and 3(b) are top and side views of conical-shaped containers 30 that may be used with the invention. The conical-shaped containers 30 similarly have cavities 31 with sloped walls to receive dispensed material 22. The bottom of the cavities may be pointed (FIG. 3(a) (conical) or flat (frusto-conical) (FIG. 3(b)).

Yet another type of shaped container 30 could be a regularly-shaped column having a regular shape, such as a pyramidal, conical or semi-spherical shape, which is cut vertically into a solid block. The volume of dispensed material 22, shaped by the walls of the shaped container 30, is equivalent to its base area multiplied by its vertical height. In this case, the preferable dispensing method is glob or dot dispensing, whereby the material 22 is dispensed from a fixed location. Other shapes of cavities or of shaped containers 30 are conceivable besides those specifically illustrated above.

Figure 4:
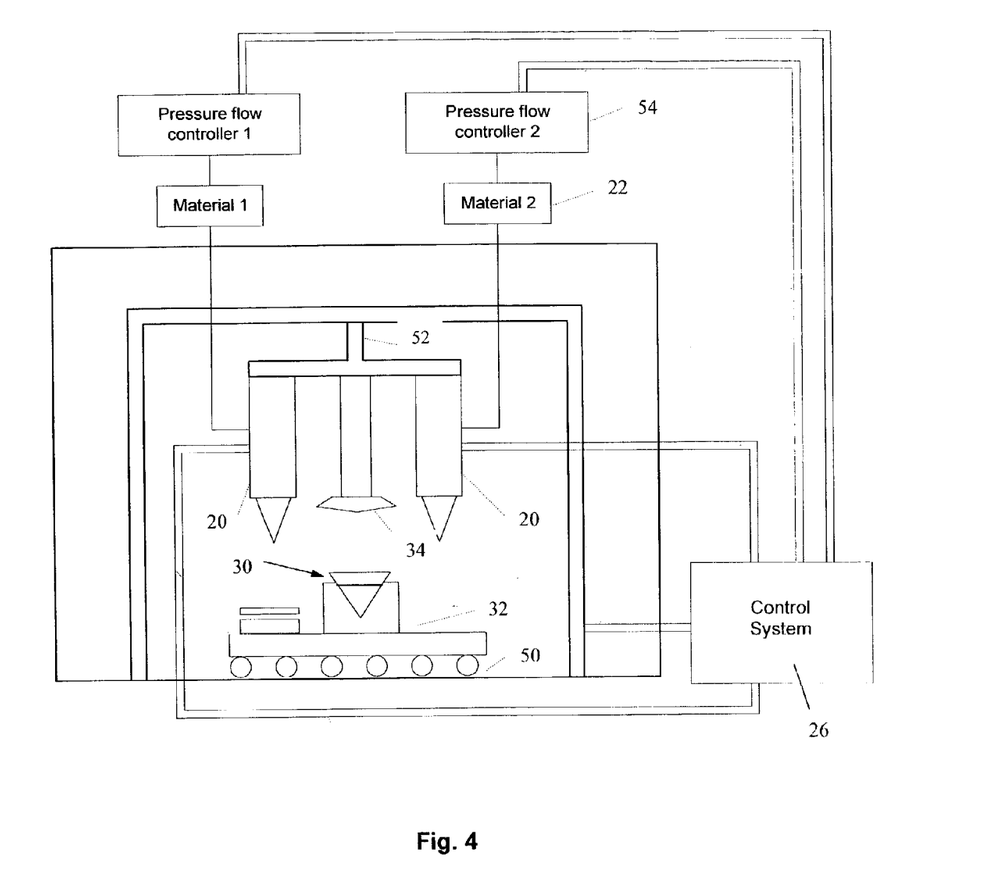
FIG. 4 is a schematic diagram showing components of an apparatus according to the preferred embodiment of the invention.

FIG. 4 is a schematic diagram showing components of an apparatus according to the preferred embodiment of the invention. The operation of the dispensing system 10 will be discussed. The dispensing system 10 may have one or two dispensers 20 in which the material 22 to be dispensed is installed and fed via a pressure flow controller 54. The computerized control system 26 dictates actuation of the dispenser 20 to govern the flow of material 22 by means of changing travel speed of a moving gantry table 52, which is usually in units of millimeters per second, and/or dispensing speed of the dispenser 20. The shaped container 30 is utilized to monitor the performance of the dispenser 20. The shaped container 30 together with its support system 32 can be loaded into a dispensing zone of the table 50 either manually or automatically with mechanical transportation.

The dispenser 20 is attached to a movable gantry table 52, wherein movements of the gantry table 52 may be computer-controlled. Movement of the gantry table 52 is in three dimensions, i.e. in the x, y and z axes. The CCD camera 34 is preferably positioned between the dispensers 20, as in FIG. 4. The CCD camera 34 is first aligned with a predetermined dispensing location directly over the shaped container 30 for positional alignment. Then, the dispenser 20 moves to extrude fluid material 22 onto the shaped container 30 according to a programmed routine. Next, the CCD camera 34 is again positioned over the shaped container 30, and simultaneously triggers a proper level of height and a suitable lighting environment such as contrast and brightness in order to provide a clear and focused image.

A number of shaped containers 30 may be implemented by having a plurality of shaped containers 30 on the supporting system 32 and/or table 50. The volume measurement may then be repeated with respect to the plurality of shaped containers 30 installed, and an average volume flow of the dispenser 20 may be calculated.

The table 50 preferably includes leveling tools and/or a temperature controller aimed at stabilization of the shaping process. The leveling tools provide a horizontal scale to prevent the fluid material from sliding to one side within the shaped container 30. In addition, shaped containers 30 in single or repeated units are also placed onto the supporting system 32 and/or table 50 in fixed positions and may be locked with mechanical means or vacuum suction.

Figure 5:
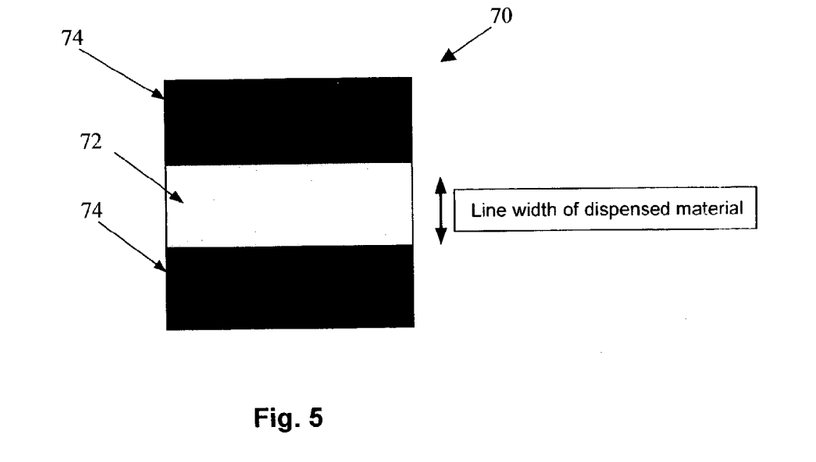
FIG. 5 is an example of a captured top-view image of a container containing dispensed material.

FIG. 5 is an example of a captured top-view image 70 of a shaped container 30 containing dispensed material 22. The image 70 comprises a strip in the form of a light band 72 (corresponding to a width of dispensed material) and dark bands 74 (corresponding to unfilled portions of the shaped container 30). The width of the dispensed material 22 is determinable by counting the number of pixels across the light band 72. The ways to locate the edges of the light band 72 include manual input and automatic operation by means of a computer-controlled imaging system.

Figure 6:
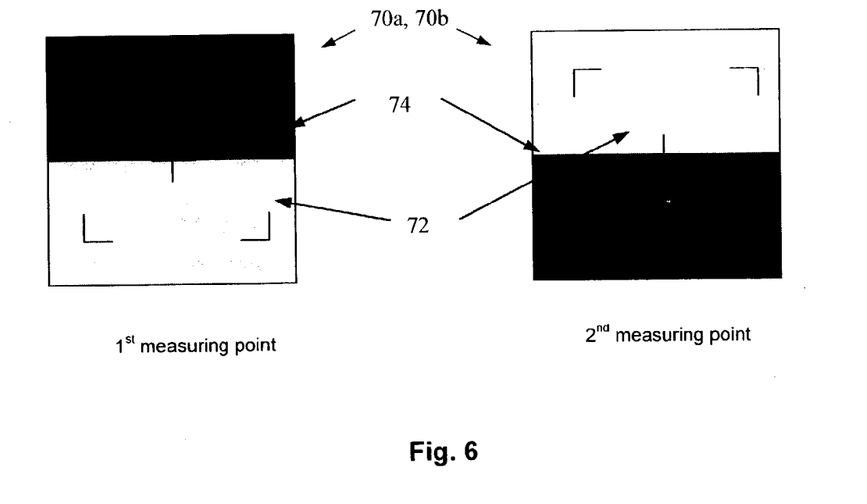
FIG. 6 is an example of captured multiple top-view images of a container containing dispensed material, where a width of a light band representative of a material's width is larger than the viewing range of a viewing camera.

FIG. 6 is an example of captured multiple top-view images 70a, 70b of a shaped container 30 containing dispensed material 22 having a light band 72 representative of the width of material 22. Two images 70a, 70b are required where the width of the light band 72 is larger than the viewing range of the CCD camera 34. The movable gantry table 52 may be used to acquire the separate images 70a, 70b. The CCD camera 34 attached to the gantry table 52 is initially moved to a first region over the shaped container 30 and captures an image 70a at a first measuring point corresponding to a first side of the light band 72 of dispensed material 22. Next, the gantry table 52 brings the CCD camera 34 to the second region over the shaped container 30 for capturing a second image 70b at the second measuring point corresponding to a second side of the light band 72. In this embodiment, the traveling distance of the gantry table 52 between the first and second measuring points represents the line width of a strip of the dispensed material 22. This distance may be obtained from encoder readings of a position encoder (not shown) associated with the gantry table 52.

Figure 7:
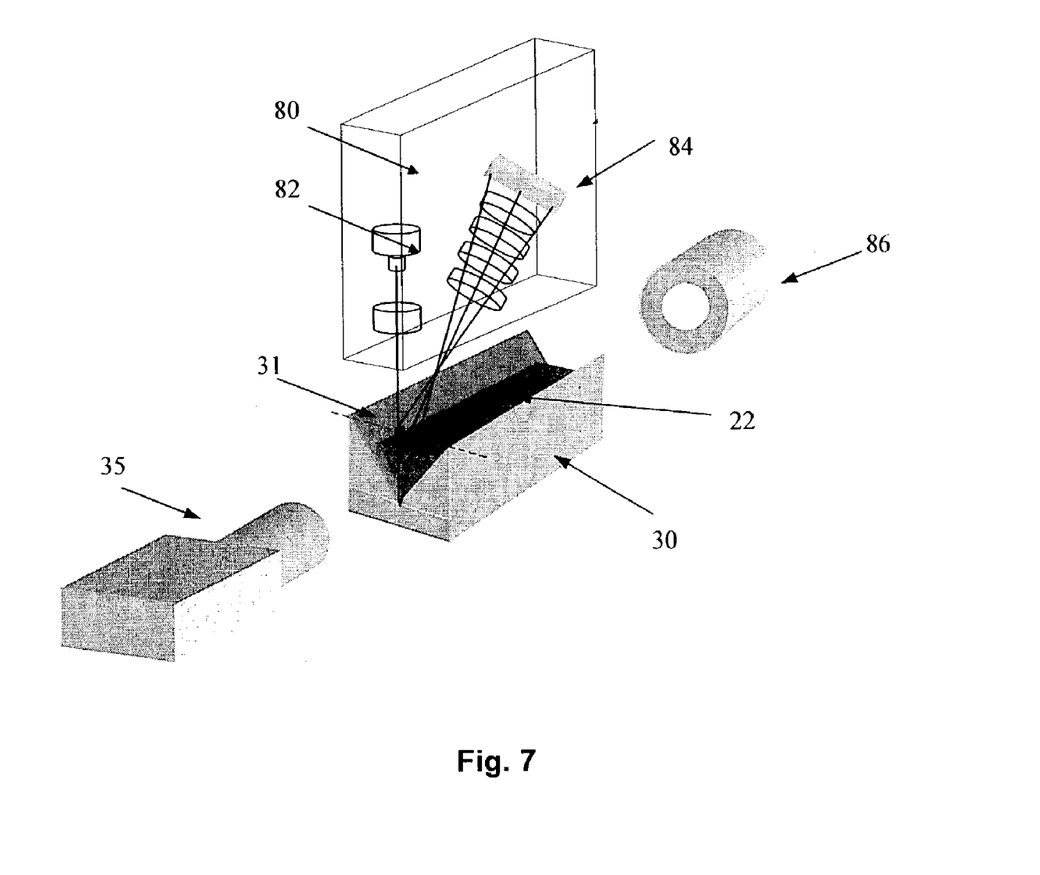
FIG. 7 is a conceptual isometric view of a laser displacement sensor and camera system useable with the invention to measure the height of dispensed material.

FIG. 7 is a conceptual isometric view of a laser displacement sensor and camera system useable with the invention to measure the height of the dispensed material 22. The apparatus measures the height of the dispensed material 22 within the confines of the shaped container 30. The laser displacement sensor comprising a laser diode 80 operates with a laser beam generated by the laser diode 80 through a transmitter lens 82, and projects the laser beam onto the surface of the material 22. The reflected laser beam is focused with a receiver lens 84 to measure the relative positions of the top and bottom points of the dispensed material 22, as depicted in FIG. 7. The distance between the top and bottom points represent the height of the material 22.

An alternative method to measure the height of the material is to capture its image with a second CCD camera 35 positioned in line with a longitudinal axis of the cavity 31 of the shaped container, with the assistance of a light source positioned along the longitudinal axis of the cavity 31, for example a back light source 86 located on an opposite side when capturing a silhouette image, to increase contrast. Alternatively, a front light source can be used. The height of the material is determined by the distance between the base and the top surface of the material 22. This can be obtained by calculating the number of vertical image pixels comprised in the portion of the captured image constituting the material 22. Another utilization of the second CCD camera 35 is to use it to measure the cross-sectional area of the material 22 within the confines of the shaped container 30, instead of just the height. The width of dispensed material 22, in addition to the height, may be expressed in image pixels to calculate the volume of dispensed material 22. This is in turn convertible to actual volume using a scaling formula.

Figure 8:
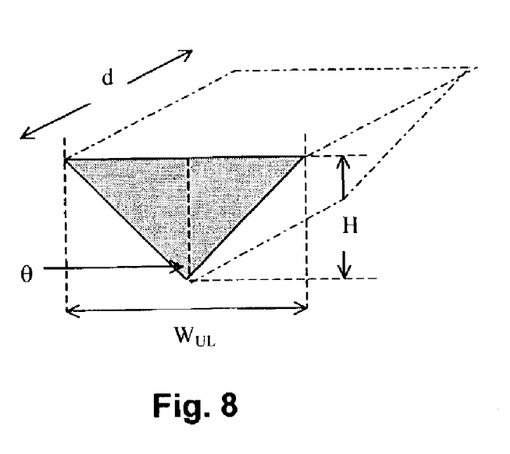
FIGS. 8 and 9 are cross-sectional views of a volume of dispensed material in a shaped container upon which an exemplary algorithm for determining a quantity of material dispensed may be based.
Figure 9:
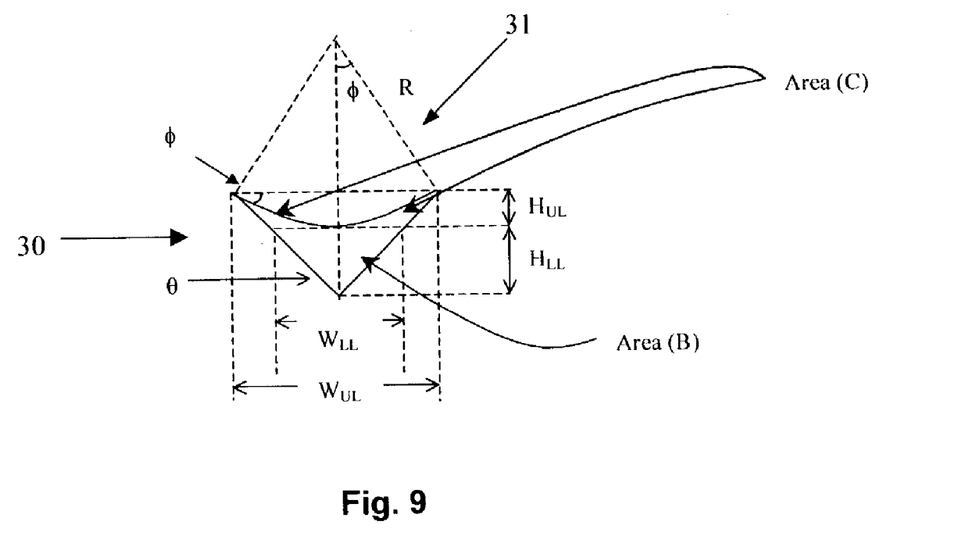

FIGS. 8 and 9 are cross-sectional views of a quantity of dispensed material in a shaped container upon which an exemplary algorithm for determining a quantity of material dispensed may be based. Referring first to FIG. 8, which illustrates measurement of a quantity of dispensed material without consideration of surface tension between the material and a V-groove cavity, $$A = \frac{1}{2} W_{UL} H \qquad (I)$$

$$\text{since } H = \frac{W_{UL}}{2\tan\theta} \qquad (II)$$

$$\text{thus, } A = \frac{W_{UL}^2}{4\tan\theta} \qquad (III)$$

$$\text{and } V = A \times d \qquad (IV)$$

where $V$ is the dispensed volume and
$d$ is the known length of the dispensed line The value of $W_{UL}$ is equal to the width of dispensed material width measured by the vision system, and the values of $\theta$ and $d$ are known geometrical dimensions of the V-groove cavity. However, as mentioned previously, the cross-sectional area of dispensed material in terms of pixels may also be measured directly with a CCD camera facing a longitudinal side of the V-groove cavity.

To increase the accuracy of measurement, consideration of surface tension between a quantity of dispensed material and a V-groove cavity is desirable. The calculations involved are illustrated with reference to FIG. 9:

$$V = [Area(B) + Area(C)] \times d \quad \text{(V)}$$

$$Area(B) = \frac{W_{LL} \cdot H_{LL}}{2} \quad \text{(VI)}$$

$$Area(C) = \frac{1}{2}\left((W_{LL} + W_{UL}) \times H_{UL} + W_{UL} \times (R - H_{UL}) - \frac{\phi \pi R^2}{90}\right) \quad \text{(VII)}$$

wherein, $$W_{LL} = 2 \cdot H_{LL} \cdot \tan\theta \quad \text{(II)}$$

$$H_{UL} = \frac{W_{UL}}{2\tan\theta} - H_{LL} \quad \text{(I)}$$

$$R = \frac{1}{2}\left(\frac{W_{UL}^2}{4H_{UL}} + H_{UL}\right) \quad \text{(III)}$$

and $$\phi = \sin^{-1}\left(\frac{W_{UL}}{2R}\right) \quad \text{(IV)}$$

Thus, the volume of the dispensed material can be obtained by measuring the width of the dispensed material, $W_{UL}$, measured by a vision system, and the height of a meniscus, $H_{LL}$, measured by the aforementioned CCD camera, laser diode, or other means. The values of $\theta$ and d are known geometrical dimensions of the V-groove cavity. The cross-sectional area of the dispensed material in terms of pixels may be also measured directly with a CCD camera as described above.

Finally, once the volume of dispensed material is found, the volume flow of the dispenser can be calculated as follows, Volume flow, $$\forall = \frac{V}{t}$$

where t is the dispensing time.

The invention described herein is susceptible to variations, modifications and/or additions other than those specifically described and it is to be understood that the invention includes all such variations, modifications and/or additions which fall within the spirit and scope of the above description.

The invention claimed is:

1. Apparatus for calibrating a dispensing system, comprising:
   a container having a cavity that is positionable under a dispenser for receiving a controlled quantity of fluid material dispensed from the dispenser into the cavity in a given time;
   an optical system operative to capture an image of a physical dimension of the quantity of dispensed material dispensed into the cavity;
   a calibrating system in communication with the optical system which is operative to calculate a volume of the quantity of material based upon said physical dimension; and
   a control system responsive to feedback obtained from the calibrating system and operative to adjust a rate of dispensation of material by the dispenser for obtaining a desired volume of dispensed material in said given time.

2. Apparatus according to claim 1, wherein the optical system is a vision system which comprises an image capturing device and an imaging system.

3. Apparatus according to claim 2, wherein the image capturing device is located above a top surface area of the cavity.

4. Apparatus according to claim 3, wherein the image capturing device is operative to capture an image containing a strip of dispensed material corresponding to a width of a top surface area of the strip of material.

5. Apparatus according to claim 3, wherein the image capturing device is operative to capture separate images from opposite edges of the top surface area of a strip of dispensed material, such that a width of the strip is equivalent to a distance moved by the image capturing device to capture said images.

6. Apparatus according to claim 2, wherein the image capturing device is located along a longitudinal axis of a length of the cavity adjacent to an end of the cavity.

7. Apparatus according to claim 6, including a light source located at an end of the cavity along the longitudinal axis of the cavity.

8. Apparatus according to claim 2, wherein the image capturing device is operative to capture an image of a portion of dispensed material expressed as a number of image pixels comprised in that portion, and convert said number of image pixels into actual volume.

9. Apparatus according to claim 1, wherein the physical dimension captured is selected from the group consisting of a width of a top surface area of dispensed material, height of a quantity of dispensed material, and cross-sectional area of a quantity of dispensed material along a length of the material-receiving cavity.

10. Apparatus according to claim 2, including a laser displacement sensor operative to generate a laser beam to measure a height of a quantity of dispensed material equivalent to a distance between top and bottom points of the dispensed material.

11. Apparatus according to claim 1, including a data storage system wherein data on physical dimensions of a quantity of dispensed material are storable.

12. Apparatus according to claim 1, wherein the cavity of the container has substantially sloping sides and has a uniform cross-sectional area.

13. Apparatus according to claim 1, wherein the cavity of the container comprises a substantially conical shape or a substantially frusto-conical shape.

14. Apparatus according to claim 1, wherein the cavity of the container comprises a column with a substantially uniform cross-sectional area.

15. Apparatus according to claim 1, including a support system onto which the container is supported, said support system comprising a table including a levelling tool and/or a temperature controller.

16. Apparatus according to claim 1, including a plurality of containers each of which is configured to receive material dispensed by the dispensing system so as to determine a mean value of a volume of material dispensed in a given time.

17. Apparatus according to claim 1, wherein the control system is configured to receive dispensing control parameters from the calibrating system, whereby the control system is operative to modify an amount of material dispensed from the dispenser based on said dispensing control parameters.

18. Apparatus according to claim 17, including a gantry table operative to support the dispenser, wherein a speed of travel of the gantry table during dispensing by the dispenser is responsive to control signals generated by the control system.

19. Apparatus according to claim 18, wherein a dispensing control parameter comprises a travelling speed of the gantry table and/or a dispensing speed of the dispenser.

20. A method for calibrating a dispensing system, comprising the steps of:
dispensing a controlled quantity of fluid material in a given time into a cavity of a container positioned under a dispenser;
capturing an image of a physical dimension of the quantity of material dispensed into the cavity;
processing the image to calculate a volume of the quantity of material in the container based upon said physical dimension; and thereafter
providing feedback to a control system regarding the volume of the material dispensed and adjusting a rate of dispensation of material by the dispenser accordingly.

21. A method according to claim 20, wherein the step of capturing an image further comprises providing a vision system including an image capturing device and an imaging system.

22. A method according to claim 21, wherein the step of capturing an image of the quantity of material further comprises the step of locating the image capturing device above a top surface area of the dispensed material in the cavity.

23. A method according to claim 22, wherein the step of capturing an image includes capturing an image containing a strip of the dispensed material corresponding to a width of a top surface area of the strip of material.

24. A method according to claim 22, wherein the step of capturing an image includes capturing separate images from opposite edges of the top surface area of a strip of dispensed material, such that a width of the strip is equivalent to a distance moved by the image capturing device to capture said images.

25. A method according to claim 21, wherein the step of capturing an image of the quantity of material further comprises the step of locating the image capturing device along a longitudinal axis of a length of the cavity adjacent to an end of the cavity.

26. A method according to claim 25, further comprising the step of positioning a light source at an end of the cavity along the longitudinal axis of the cavity.

27. A method according to claim 21, wherein the step of processing the image further comprises measuring a portion of dispensed material in terms of a number of image pixels comprised in that portion, and converting said number of image pixels into actual volume.

28. A method according to claim 20, wherein the physical dimension captured is selected from the group consisting of a width of a top surface area of dispensed material, height of a quantity of dispensed material, and cross-sectional area of a quantity of dispensed material along a length of the material-receiving cavity.

29. A method according to claim 28, wherein the step of processing the image further comprises taking into account surface tension due to adhesion of the material to a surface of the cavity when calculating volume.

30. A method according to claim 21, further comprising the step of generating a laser beam by way of a laser displacement sensor to measure a height of a quantity of dispensed material equivalent to a distance between top and bottom points of the dispensed material before processing the captured image.

31. A method according to claim 20, further comprising the step of storing data on physical dimensions of a quantity of dispensed material into a data storage system.

32. A method according to claim 31, further comprising the step of retrieving stored data to determine certain physical dimensions of a quantity of dispensed material corresponding to a physical dimension of a type of material captured by the vision system.

33. A method according to claim 20, wherein the cavity of the container has substantially sloping sides and has a uniform cross-sectional area.

34. A method according to claim 20, wherein the cavity of the container comprises a substantially conical shape or a substantially frusto-conical shape.

35. A method according to claim 20, wherein the cavity of the container comprises a column with a uniform cross-sectional area.

36. A method according to claim 20, further comprising the step of repeated dispensing of material into a plurality of containers and determining a mean value of volume of material dispensed in a given time.

37. A method according to claim 20, wherein the step of providing feedback regarding the volume of material dispensed further comprises sending dispensing control parameters to the control system, whereby the control system is operative to modify a rate at which material is dispensed from the dispensing system.

38. A method according to claim 37, wherein dispensing control parameters are sent continuously in real time to the control system as material is dispensed into the container.

39. A method according to claim 38, further comprising the step of supporting the dispenser on a gantry table, and controlling a speed of the gantry table during dispensing by the dispenser in response to control signals generated by the control system.

40. A method according to claim 38, further comprising the step of supporting the dispenser on a gantry table, and controlling dispensing speed of the dispenser during dispensing by the dispenser in response to control signals generated by the control system.

41. A method according to claim 40, wherein a dispensing control parameter comprises a travelling speed of the gantry table and/or dispensing speed of the dispenser.

42. In combination, the apparatus of claim 1 and a dispenser disposed above the container cavity and the dispenser being operable to dispense the quantity of material into the cavity in a given time.

* * * * *